US008871994B2

(12) United States Patent
Wei et al.

(10) Patent No.: US 8,871,994 B2
(45) Date of Patent: Oct. 28, 2014

(54) WETNESS SENSOR FOR USE IN AN ABSORBENT ARTICLE

(75) Inventors: Ning Wei, Roswell, GA (US); Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 661 days.

(21) Appl. No.: 12/964,811

(22) Filed: Dec. 10, 2010

(65) Prior Publication Data

US 2012/0150134 A1    Jun. 14, 2012

(51) Int. Cl.
*A61F 13/15* (2006.01)
*A61L 15/56* (2006.01)

(52) U.S. Cl.
CPC ...................................... *A61L 15/56* (2013.01)
USPC ........................................................... 604/361

(58) Field of Classification Search
CPC ........................... A61F 13/42; A61F 2013/422
USPC .......................................................... 604/361
See application file for complete search history.

(56) References Cited

U.S. PATENT DOCUMENTS

| 4,425,161 A | 1/1984 | Shibahashi et al. |
| 4,482,378 A | 11/1984 | Riou et al. |
| 4,557,618 A | 12/1985 | Iwata et al. |
| 4,620,941 A | 11/1986 | Yoshikawa et al. |
| 4,717,710 A | 1/1988 | Shimizu et al. |
| 4,957,949 A | 9/1990 | Kamada et al. |
| 5,008,238 A | 4/1991 | Gotoh et al. |
| 5,024,699 A | 6/1991 | Llyama et al. |
| 5,130,290 A | 7/1992 | Tanimoto |
| 5,197,958 A | 3/1993 | Howell |
| 5,281,570 A | 1/1994 | Hasegawa et al. |
| 5,350,634 A | 9/1994 | Sumii et al. |
| 5,389,093 A | 2/1995 | Howell |

(Continued)

FOREIGN PATENT DOCUMENTS

| EP | 0 788 889 B1 | 8/1997 |
| EP | 2067458 A1 * | 6/2009 |

(Continued)

OTHER PUBLICATIONS

Abstract of Japanese Patent—JP58023864 dated Feb. 12, 1983, 1 page.

(Continued)

*Primary Examiner* — Melanie Hand
*Assistant Examiner* — Aundria Hairell
(74) *Attorney, Agent, or Firm* — Dority & Manning, P.A.

(57) ABSTRACT

A wetness sensor for an absorbent article that is formed from an ink is provided. The ink includes a proton-accepting chromogen and a proton-donating agent (or color developer). Prior to use, the ink is generally dry and in a protonated form so that it has a visible color. However, upon contact with bodily fluids (e.g., urine, fecal matter, mucus, menses, vaginal fluid, etc.), water in the fluid can lead to deprotonation of the chromogen, thereby resulting in a shift of the absorption maxima of the chromogen towards either the red ("bathochromic shift") or blue end of the spectrum ("hypsochromic shift"). To increase the rate of the color change during use, the proton-donating agent is an aliphatic carboxylic acid that is highly soluble in the bodily fluid (e.g., urine), and therefore results in a color change that is very rapid and may be detected within a relatively short period of time.

25 Claims, 2 Drawing Sheets

(56) References Cited

U.S. PATENT DOCUMENTS

| | | |
|---|---|---|
| 5,413,629 A | 5/1995 | Yasui et al. |
| 5,415,434 A | 5/1995 | Kawashima |
| 5,417,748 A | 5/1995 | Kawashima |
| 5,431,697 A | 7/1995 | Kamata et al. |
| 5,485,792 A | 1/1996 | Keyser et al. |
| 5,527,385 A | 6/1996 | Sumii et al. |
| 5,649,828 A | 7/1997 | Kawashima |
| 5,681,380 A | 10/1997 | Nohr et al. |
| 5,753,587 A | 5/1998 | Podszun et al. |
| 6,300,277 B1 | 10/2001 | Miyauchi et al. |
| 6,527,384 B2 | 3/2003 | Isago |
| 6,793,721 B2 | 9/2004 | Shen et al. |
| 6,863,720 B2 | 3/2005 | Kitagawa et al. |
| 6,875,798 B2 | 4/2005 | Yui et al. |
| 6,890,614 B2 | 5/2005 | Gore et al. |
| 7,105,715 B2 | 9/2006 | Carlucci et al. |
| 7,159,532 B2 | 1/2007 | Klofta et al. |
| 7,280,441 B2 | 10/2007 | MacDonald et al. |
| 7,294,182 B2 | 11/2007 | Jang et al. |
| 7,370,689 B2 | 5/2008 | Wang |
| 7,489,252 B2 | 2/2009 | Long et al. |
| 7,635,662 B2 | 12/2009 | Kabashima et al. |
| 7,642,218 B2 | 1/2010 | Risch et al. |
| 7,648,842 B2 | 1/2010 | Hartlep |
| 7,727,319 B2 | 6/2010 | Li et al. |
| 7,763,442 B2 | 7/2010 | Martin et al. |
| 8,080,704 B2 | 12/2011 | Uchida et al. |
| 8,088,966 B2 | 1/2012 | Matsui |
| 8,097,389 B2 | 1/2012 | Nakamura |
| 8,134,042 B2 | 3/2012 | Song et al. |
| 8,222,476 B2 | 7/2012 | Song et al. |
| 8,273,939 B2 | 9/2012 | Klofta et al. |
| 8,348,920 B2 | 1/2013 | Liu |
| 2002/0061819 A1 | 5/2002 | Ohno |
| 2003/0087566 A1 | 5/2003 | Carlyle et al. |
| 2004/0087922 A1 | 5/2004 | Bobadilla |
| 2004/0116213 A1 | 6/2004 | Filosa et al. |
| 2006/0287215 A1 | 12/2006 | McDonald et al. |
| 2007/0015092 A1 | 1/2007 | Gore et al. |
| 2007/0252115 A1 | 11/2007 | Arehart et al. |
| 2007/0265591 A1 | 11/2007 | Loritz et al. |
| 2007/0270773 A1 | 11/2007 | Mackey |
| 2008/0113862 A1 | 5/2008 | Stovold et al. |
| 2008/0214392 A1 | 9/2008 | Gore et al. |
| 2008/0248950 A1 | 10/2008 | Katampe et al. |
| 2009/0124497 A1 | 5/2009 | Nakatsubo et al. |
| 2009/0143516 A1 | 6/2009 | MacDonald et al. |
| 2009/0157023 A1* | 6/2009 | Song et al. ............... 604/361 |
| 2009/0157024 A1* | 6/2009 | Song ............... 604/361 |
| 2009/0215621 A1 | 8/2009 | Jackson |
| 2009/0221980 A1 | 9/2009 | Mosbacher et al. |
| 2009/0275908 A1* | 11/2009 | Song ............... 604/361 |
| 2009/0325221 A1 | 12/2009 | Long et al. |
| 2009/0326409 A1 | 12/2009 | Cohen et al. |
| 2010/0012017 A1 | 1/2010 | Miller |
| 2010/0021702 A1 | 1/2010 | Wakasugi et al. |
| 2010/0030173 A1 | 2/2010 | Song et al. |
| 2011/0144603 A1 | 6/2011 | Song |
| 2012/0150134 A1 | 6/2012 | Wei et al. |

FOREIGN PATENT DOCUMENTS

| | | |
|---|---|---|
| GB | 531312 | 1/1941 |
| WO | WO 2006/039515 A2 | 4/2006 |
| WO | WO 2006/039515 A3 | 4/2006 |
| WO | WO 2008/026105 A2 | 3/2008 |
| WO | WO 2008/026105 A3 | 3/2008 |

OTHER PUBLICATIONS

Abstract of Japanese Patent—JP58128892 dated Aug. 1, 1983, 1 page.
Abstract of Japanese Patent—JP63264683 dated Nov. 1, 1988, 1 page.
Abstract of Japanese Patent—JP4085374 dated Mar. 18, 1992, 1 page.
Abstract of Japanese Patent—JP4239064 dated Aug. 26, 1992, 1 page.
Abstract of Japanese Patent—JP6092016 dated Apr. 5, 1994, 1 page.
Abstract of Japanese Patent—JP6316152 dated Nov. 15, 1994, 2 pages.
Abstract of Japanese Patent—JP7090213 dated Apr. 4, 1995, 1 page.
Abstract of Japanese Patent—JP8058230 dated Mar. 5, 1996, 2 pages.
Abstract of Japanese Patent—JP8060065 dated Mar. 5, 1996, 2 pages.
Abstract of Japanese Patent—JP9165537 dated Jun. 24, 1997, 1 page.
Abstract of Japanese Patent—JP10077437 dated Mar. 24, 1998, 1 page.
Abstract of Japanese Patent—JP10287081 dated Oct. 27, 1998, 2 pages.
Abstract of Japanese Patent—JP2001247807 dated Sep. 14, 2001, 1 page.
Abstract of Japanese Patent—JP2001279144 dated Oct. 10, 2001, 1 page.
Abstract of Japanese Patent—JP2001311024 dated Nov. 9, 2001, 2 pages.
Abstract of Japanese Patent—JP2001342415 dated Dec. 14, 2001, 1 page.
Abstract of Japanese Patent—JP2004001413 dated Jan. 8, 2004, 2 pages.
Abstract of Japanese Patent—JP2004244453 dated Sep. 2, 2004, 2 pages.
Abstract of Japanese Patent—JP2005089614 dated Apr. 7, 2005, 1 page.
Abstract of Japanese Patent—JP2006022214 dated Jan. 26, 2006, 1 page.
Abstract of Japanese Patent—JP2006022215 dated Jan. 26, 2006, 1 page.
Abstract of Japanese Patent—JP2006045408 dated Feb. 16, 2006, 2 pages.
Abstract of Japanese Patent—JP2008007635 dated Jan. 17, 2008, 2 pages.
Abstract of WO Patent—WO 00/29036 dated May 25, 2000, 1 page.
Abstract of WO Patent—WO 2007/004629 dated Jan. 11, 2007, 1 page.
ASTM Designation: E 1164-02—*Standard Practice for Obtaining Spectrometric Data for Object-Color Evaluation*, Aug. 2002, 8 pages.
Colorimetry, 2nd Edition, International Commission on Illumination, No. 15.2, 1986.
Japanese Industrial Standard, JIS Z 8722:2000, *Methods of colour measurement—Reflecting and transmitting objects*, Revised May 20, 2000.
Paints and Varnishes—Colorimetry—Part 1: Principles, International Standard ISO 7724/1-1984 (E), Oct. 1, 1984.
*Pocket Guide to Digital Printing*, Frank Cost, Delmar Publishers, Albany, NY, ISBN 0-8273-7592-1, pp. 144-145.
Search Report and Written Opinion for PCT/IB2011/054837 dated Jun. 25, 2012, 11 pages.

\* cited by examiner

WETNESS SENSOR FOR USE IN AN ABSORBENT ARTICLE

BACKGROUND OF THE INVENTION

The ability to sense wetness in a disposable absorbent article (e.g., diaper, training pants, incontinence pad, etc.) has been a desirable feature for a variety of modern hygiene products. Because these articles are so absorbent, for example, wearers may not realize they have urinated, particularly if they are inexperienced toddlers who may not recognize the meaning of body sensations associated with urination. Thus, the wearer may not recognize their urination control failure or be aware the article should be changed. Furthermore, parents or caregivers may not recognize that the absorbent article requires changing. Various attempts have been made to solve the problems noted above. U.S. Patent Publication No. 2010/0030173 to Song, et al., for example, describes a wetness sensor formed from a leuco dye and color developer (e.g., zinc salicylate) that exhibits a visual signal in a dry state. Upon contact with a bodily fluid, such as urine, the signal begins to fade or completely disappear. Unfortunately, such sensors often require the use of a surfactant to achieve sufficient wetting on the surface of the absorbent article, which increases the costs and complexity of the sensor. Furthermore, such sensors are also relatively insensitive to small amounts of fluids, and they can sometimes take a long time to undergo the desired color change.

As such, a need currently exists for an improved wetness sensor that can undergo a rapid color change in the present of bodily fluids.

SUMMARY OF THE INVENTION

In accordance with one embodiment of the present invention, an absorbent article is disclosed that comprises a substantially liquid impermeable layer, a liquid permeable layer, and an absorbent core positioned between the substantially liquid impermeable layer and the liquid permeable layer. A wetness sensor is integrated into the article and positioned such that the sensor is in fluid communication with a bodily fluid from a wearer of the article. The wetness sensor includes an ink comprising a proton-accepting chromogen and a proton-donating agent that includes an aliphatic carboxylic acid. The ink undergoes a visible color change upon contact with the bodily fluid.

In accordance with another embodiment of the present invention, a wetness sensor for an absorbent article is disclosed that comprises an ink disposed on a substrate. The ink comprises a leuco dye and a proton-donating agent that includes an aliphatic carboxylic acid having a solubility in water of greater than about 5 grams per 100 milliliters of water at a temperature of 20° C. and a first acid dissociation constant of from about 0 to about 10. The ink undergoes a visible color change upon contact with an aqueous fluid.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
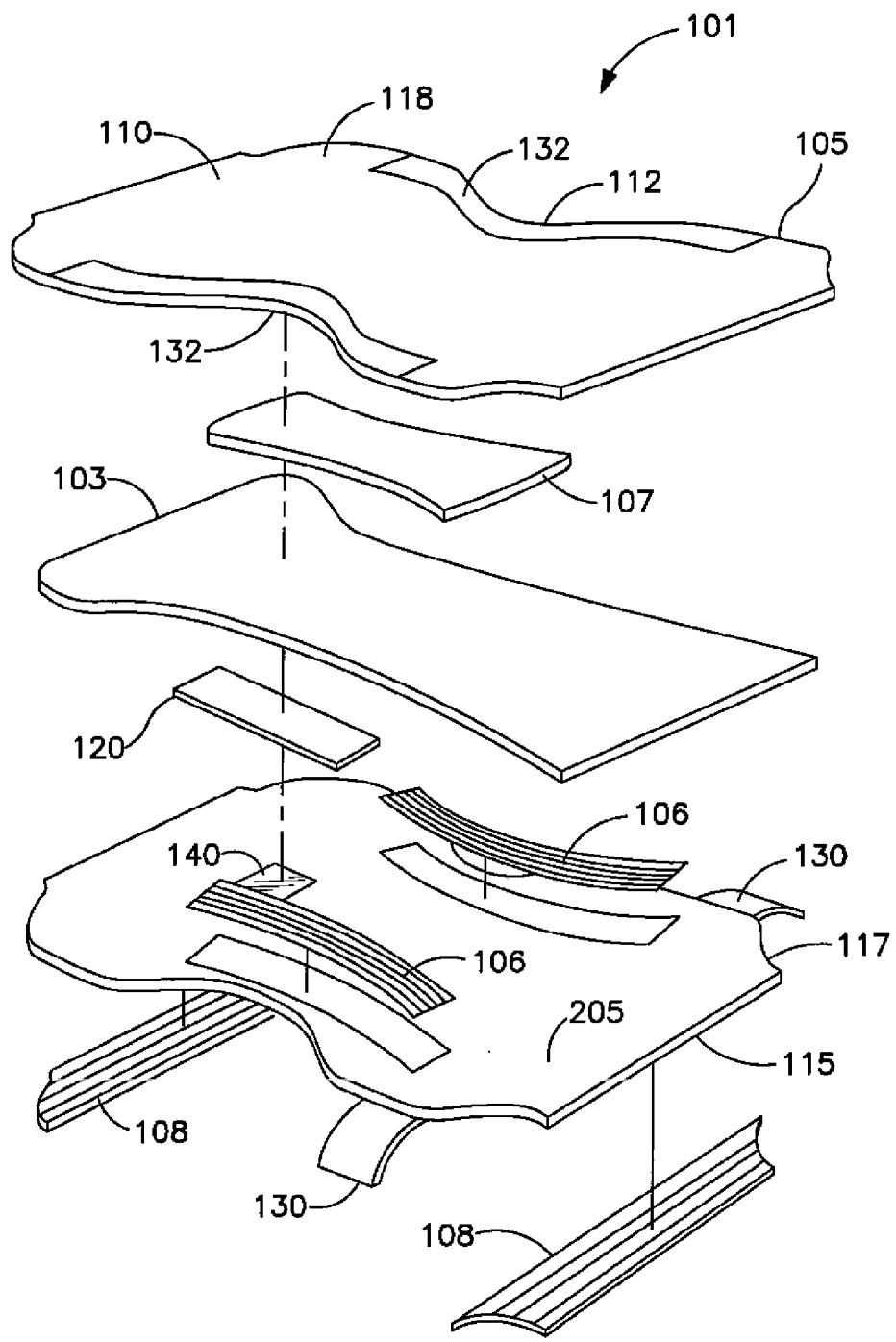
FIG. 1 is a top view of one embodiment of an absorbent article that may be used in conjunction with the wetness sensor of the present invention.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a wetness sensor for an absorbent article that is formed from an ink. The ink includes a proton-accepting chromogen and a proton-donating agent (or color developer). Prior to use, the ink is generally dry and in a protonated form so that it has a visible color. However, upon contact with bodily fluids (e.g., urine, fecal matter, mucus, menses, vaginal fluid, etc.), water in the fluid can lead to deprotonation of the chromogen, thereby resulting in a shift of the absorption maxima of the chromogen towards either the red ("bathochromic shift") or blue end of the spectrum ("hypsochromic shift"). The nature of the color change depends on a variety of factors, including the type of proton-accepting chromogen and the presence of any additional temperature-insensitive chromogens. In one embodiment, for example, the ink has a visually observable color in its dry state that fades or disappears upon contact with a bodily fluid.

To increase the rate of the color change during use, the present inventors have discovered that a specific type of proton-donating agent may be employed. More particularly, the proton-donating agent is an aliphatic carboxylic acid that is highly soluble in the bodily fluid (e.g., urine), and therefore results in a color change that is very rapid and may be detected within a relatively short period of time. For example, a visual change in color may occur in about 30 seconds or less, in some embodiments about 15 seconds or less, and in some embodiments, about 5 seconds or less. The extent of the color change is also generally sufficient to provide a "real-time" indication of wetness on the absorbent article. This color change may, for example, be represented by a certain change in the absorbance reading as measured using a conventional test known as "CIELAB", which is discussed in *Pocket Guide to Digital Printing* by F. Cost, Delmar Publishers, Albany, N.Y. ISBN 0-8273-7592-1 at pages 144 and 145. This method defines three variables, L*, a*, and b*, which correspond to three characteristics of a perceived color based on the opponent theory of color perception. The three variables have the following meaning:

L*=Lightness (or luminosity), ranging from 0 to 100, where 0=dark and 100=light;

a*=Red/green axis, ranging approximately from −100 to 100; positive values are reddish and negative values are greenish; and b*=Yellow/blue axis, ranging approximately from −100 to 100; positive values are yellowish and negative values are bluish.

Because CIELAB color space is somewhat visually uniform, a single number may be calculated that represents the difference between two colors as perceived by a human. This difference is termed ΔE and calculated by taking the square root of the sum of the squares of the three differences (ΔL*, Δa*, and Δb*) between the two colors. In CIELAB color space, each ΔE unit is approximately equal to a "just noticeable" difference between two colors. CIELAB is therefore a good measure for an objective device-independent color specification system that may be used as a reference color space for the purpose of color management and expression of changes in color. Using this test, color intensities (L*, a*, and b*) may thus be measured using, for instance, a handheld spectrophotometer from Minolta Co. Ltd. of Osaka, Japan (Model #CM2600d). This instrument utilizes the D/8 geometry conforming to CIE No. 15, ISO 7724/1, ASTME1164 and JIS 28722-1982 (diffused illumination/8-degree viewing system. The D65 light reflected by the specimen surface at an angle of 8 degrees to the normal of the surface is received by the specimen-measuring optical system. Typically, the color change is represented by a ΔE of about 2 or more, in some embodiments about 3 or more, and in some embodiments, from about 5 to about 50.

As indicated above, the aliphatic carboxylic acid of the present invention is highly soluble in the bodily fluid so that the resulting color change will be rapid and easily detected by the user or wearer. Because bodily fluids generally contain a substantial amount of water, the acid will also typically exhibit a high water solubility, such as greater than about 5 grams per 100 milliliters of water, in some embodiments greater than about 15 grams per 100 milliliters of water, in some embodiments, from about 30 to about 200 grams per 100 milliliters of water, and in some embodiments, from about 50 grams to about 150 grams per 100 milliliters of water, determined at a temperature of 20° C. In addition to being highly soluble in water, however, the acid is also generally considered "weak" so that it may safely contact the skin of a wearer, but yet strong enough to achieve the desired pH level. In this regard, the acid typically has a first acid dissociation constant ($pK_{a1}$) of about 0 to about 8, in some embodiments about 0.5 to about 6, and in some embodiments, from about 1 to about 5, determined at 25° C. This may result in a pH level for the ink of about 5 or less, and in some embodiments, from about 1 to about 4.

Suitable aliphatic carboxylic acids having the characteristics noted above may include, for instance, acrylic acid, methacrylic acid, malonic acid, succinic acid, adipic acid, maleic acid, malic acid, oleic acid, tartaric acid (e.g., dextotartaric acid, mesotartaric acid, etc.), citric acid, formic acid, acetic acid, glycolic acid, oxalic acid, propionic acid, glutaric acid, gluconic acid, lactic acid, aspartic acid, glutaminic acid, itaconic acid, trifluoroacetic acid, etc. Polymeric acids, such as poly(acrylic) or poly(methacrylic) acid and copolymers thereof (e.g., maleic-acrylic, sulfonic-acrylic, and styrene-acrylic copolymers), may also be suitable for use in the present invention. Particularly suitable acids are polyprotic acids (e.g., diprotic, triprotic, etc.), such as α-tartaric acid ($pk_{a1}$ of 2.98 and $pK_{a2}$ of 4.34, solubility of 133 grams per 100 millimeters of water), oxalic acid ($pK_{a1}$ of 1.23 and $pK_{a2}$ of 4.19, solubility of 90 grams per 100 millimeters of water), citric acid ($pK_{a1}$ of 3.13, $pK_{a2}$ of 4.76, and $pK_{a3}$ of 6.40, solubility of 73 grams per 100 millimeters of water), etc.

Any of a variety of proton-accepting chromogens may generally be employed in the ink. One particularly suitable class of proton-accepting chromogens are leuco dyes, which are desirably colorless in their deprotonated form. Suitable leuco dyes may include, for instance, phthalides, phthalanes, acyl-leucomethylene compounds, fluoranes, spiropyranes, cumarins, etc., as well as mixtures of any of the foregoing. Exemplary fluoranes include, for instance, 3,3'-dimethoxy-fluorane, 3,6-dimethoxyfluorane, 3,6-di-butoxyfluorane, 3-chloro-6-phenylamino-flourane, 3-diethylamino-6-dimethylfluorane, 3-diethylamino-6-methyl-7-chlorofluorane, and 3-diethyl-7,8-benzofluorane, 3,3'-bis-(p-dimethyl-aminophenyl)-7-phenylaminofluorane, 3-diethylamino-6-methyl-7-phenylamino-fluorane, 3-diethylamino-7-phenyl-aminofluorane, and 2-anilino-3-methyl-6-diethylamino-fluorane. Likewise, exemplary phthalides include 3,3',3"-tris (p-dimethylamino-phenyl)phthalide, 3,3'-bis(p-dimethyl-aminophenyl)phthalide, 3,3-bis (p-diethylamino-phenyl)-6-dimethylamino-phthalide, 3-(4-diethylaminophenyl)-3-(1-ethyl-2-methylindol-3-yl)phthalide, and 3-(4-diethylamino-2-methyl)phenyl-3-(1,2-dimethylindol-3-yl)phthalide. Still other suitable chromogens are described in U.S. Pat. No. 4,620,941 to Yoshikawa, et al.; U.S. Pat. No. 5,281,570 to Hasegawa, et al.; U.S. Pat. No. 5,350,634 to Sumii, et al.; and U.S. Pat. No. 5,527,385 to Sumii, et al., which are incorporated herein in there entirety for all purposes.

The relative amount of the proton-accepting chromogen(s) and proton-donating agent(s) may vary to achieve the desired color change. Namely, the proton-donating agent is employed in an amount high enough to achieve the desired rapid color change, but not so high as to adversely impact the ability of the chromogen to remain visible prior to use. In this regard, the weight ratio of the proton-donating agent to the chromogen is typically from about 0.4 to about 10, in some embodiments from about 0.5 to about 8, and in some embodiments, from about 1 to about 4. For example, proton-donating agents may constitute from about 5 wt. % to about 60 wt. %, in some embodiments from about 10 wt. % to about 50 wt. %, and in some embodiments, from about 15 wt. % to about 40 wt. %, of the ink on a dry basis. Likewise, chromogens may constitute from about 40 wt. % to about 95 wt. %, in some embodiments from about 50 wt. % to about 90 wt. %, and in some embodiments, from about 60 wt. % to about 85 wt. %, of the ink on a dry basis.

The ink may also contain a variety of optional components to facilitate the desired color change, and also to enhance the ability of the ink to remain stable on a substrate to which it is applied. Organic binders may, for instance, be employed to increase the durability of the ink and help form stable films on various substrates upon drying. Because the ink is intended for contact with aqueous bodily fluids (e.g., urine), it is sometimes desired that hydrophobic organic binders are employed. One example of such a binder is a thermoset resin that is capable of hardening upon application to the substrate. Suitable thermoset resins may include, for instance, polyester resins, polyurethane resins, melamine resins, epoxy resins, diallyl phthalate resins, vinylester resins, and so forth. In addition or in conjunction with such hydrophobic binders, the ink may also contain a hydrophilic binder, such as alginic acid and salts thereof, carrageenan, pectin, gelatin and the like, semisynthetic macromolecular compounds, such as methylcellulose, cationized starch, carboxymethylcellulose, carboxymethylated starch, vinyl polymers (e.g., polyvinyl alcohol), polyvinylpyrrolidone, polyacrylic acid, polyacrylamide, maleic acid copolymers, cellulose acetate, cellulose butyrate, etc., as well as combination thereof. Commercially available binder systems that may be employed include, for instance, the GANTREZ® SP, ES, or AN series of monoalkyl esters of poly(methyl vinyl ether/maleic acid)

(International Specialty Products, Inc.), the DERMACRYL® series of carboxylated acrylic copolymers (Akzo Nobel), and the AMPHOMER® series of amphoteric acrylic copolymers (Akzo Nobel).

The total concentration of binders may generally vary depending on the desired properties of the resulting substrate. For instance, high total binder concentrations may provide better physical properties for the coated substrate, but may likewise have an adverse affect on other properties, such as the absorptive capacity of the substrate to which it is applied. Conversely, low total binder concentrations may not provide the desired degree of durability. Thus, in most embodiments, the total amount of binder employed in the ink, including any hydrophilic or hydrophobic binders, is from about 0.01 wt. % to about 10 wt. %, in some embodiments from about 0.05 wt. % to about 5 wt. %, and in some embodiments, from about 0.1 wt. % to about 4 wt. %, on a dry weight basis. For example, hydrophilic binders may constitute from about 0.001 wt. % to about 10 wt. %, in some embodiments from about 0.01 wt. % to about 5 wt. %, and in some embodiments, from about 0.1 wt. % to about 2 wt. %, on a dry weight basis. Likewise, hydrophobic binders may constitute from about 0.001 wt. % to about 10 wt. %, in some embodiments from about 0.01 wt. % to about 5 wt. %, and in some embodiments, from about 0.1 wt. % to about 2 wt. %, on a dry weight basis.

The ink may also contain other components as is known in the art. For example, depending on the particular nature of the substrate, the ink may include a wetting agent to improve its ability to be applied and adhered to a substrate. Suitable wetting agents may include, for instance, a surfactant (e.g., nonionic, cationic, anionic, or zwitterionic) or a mixture of surfactants. The surfactants may also help enhance the sensitivity and contrast provided by the colorant. Particularly desired surfactants are nonionic surfactants, such as ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, acetylenic diols, and mixtures thereof. Various specific examples of suitable nonionic surfactants include, but are not limited to, methyl gluceth-10, PEG-20 methyl glucose distearate, PEG-20 methyl glucose sesquistearate, $C_{11}$-$C_{15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty (C.sub.6-C.sub.22) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the SURFYNOL® range of acetylenic diol surfactants available from Air Products and Chemicals of Allentown, Pa. and the TWEEN® range of polyoxyethylene surfactants available from Fischer Scientific of Pittsburgh, Pa. While such wetting agents may be employed, it is typically desired that the ink is formed without the use of agents. Not only does this enhance manufacturing efficiency, but it also reduces the cost of the ink. While the composition may be generally free of such wetting agents, it should of course be understood that a small amount may still be present in the resulting composition. Regardless, the ink typically contains wetting agents in an amount less than about 10 wt. %, in some embodiments less than about 5 wt. %, and in some embodiments, from about 0.01 wt. % to about 2 wt. %.

Although not required, additional components can also be employed within the ink to facilitate its ability to be immobilized on a substrate. For example, an anchoring compound can be employed that links the ink to the surface of substrate and further improves durability. Typically, the anchoring compound is larger in size than the chromogen or proton-donating agent, which improves their likelihood of remaining on the surface during use. For example, the anchoring compound can include a macromolecular compound, such as a polymer, oligomer, dendrimer, particle, etc. Polymeric anchoring compounds can be natural, synthetic, or combinations thereof. Examples of natural polymeric anchoring compounds include, for instance, polypeptides, proteins, DNA/RNA and polysaccharides (e.g., glucose-based polymers, activated dextran, etc). In some embodiments, the anchoring compound can be a particle (sometimes referred to as a "bead" or "microbead"). Naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., can be used. Further, synthetic particles can also be utilized. For example, in one embodiment, latex microparticles are utilized. Although any synthetic particle can be used, the particles are typically formed from polystyrene, butadiene styrenes, styreneacrylic-vinyl terpolymer, polymethylmethacrylate, polyethyl methacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the size of the particles may vary. For instance, the average size (e.g., diameter) of the particles can range from about 0.1 nanometers to about 1,000 microns, in some embodiments, from about 0.1 nanometers to about 100 microns, and in some embodiments, from about 1 nanometer to about 10 microns.

Humectants may also be utilized, such as ethylene glycol; diethylene glycol; glycerine; polyethylene glycol 200, 300, 400, and 600; propane 1,3 diol; propylene-glycolmonomethyl ethers, such as Dowanol PM (Gallade Chemical Inc., Santa Ana, Calif.); polyhydric alcohols; or combinations thereof. Further, additional temperature-insensitive chromogens may also be employed to help control the color that is observed during use of the ink. Other additives may also be included to improve ink performance, such as a chelating agent to sequester metal ions that could become involved in chemical reactions over time and/or a corrosion inhibitor to help protect metal components of the printer or ink delivery system. Various other components for use in an ink, such as colorant stabilizers, photoinitiators, fillers, etc., may be employed as described in U.S. Pat. No. 5,681,380 to Nohr, et al. and U.S. Pat. No. 6,542,379 to Nohr, et al., which are incorporated herein in their entirety by reference thereto for all purposes.

The ink of the present invention is typically applied to a substrate. The substrate may function simply as a physical carrier for the ink, or it may perform other functions of the absorbent article into which it is incorporated. To apply the ink, the components are first typically dissolved or dispersed in a solvent to form a coating solution. For example, one or more of the above-mentioned components may be mixed with a solvent, either sequentially or simultaneously, to form an ink that may be easily applied to a substrate. Any solvent capable of dispersing or dissolving the components is suitable. Typically, however, an organic solvent is employed so that the chromogen is not deprotonated before contact with the bodily fluid. Suitable organic solvents may include, for instance, alcohols, such as ethanol or methanol; dimethylformamide; dimethyl sulfoxide; hydrocarbons, such as pentane, butane, heptane, hexane, toluene and xylene; ethers such as diethyl ether and tetrahydrofuran; ketones and aldehydes, such as acetone and methyl ethyl ketone; halogenated solvents, such as dichloromethane and carbon tetrachloride; acrylonitrile; etc., as well as mixtures thereof. The concentration of solvent in the coating formulation is generally high enough to allow easy application, handling, etc.

When employed, the total concentration of solvent(s) may vary, but is typically from about 30 wt. % to about 99 wt. %, in some embodiments from about 40 wt. % to about 95 wt. %, and in some embodiments, from about 50 wt. % to about 90 wt. % of the coating formulation. Of course, the specific amount of solvent(s) employed depends in part on the desired solids content and/or viscosity of the formulation. For example, the solids content may range from about 0.01 wt. % to about 30 wt. %, in some embodiments from about 0.1 wt. % to about 25 wt. %, and in some embodiments, from about 0.5 wt. % to about 20 wt. %. By varying the solids content, the presence of the color changing chromogen may be controlled. For example, to form an ink with a higher level of the chromogen, the formulation may be provided with a relatively high solids content so that a greater percentage of the chromogen is incorporated into the ink. In addition, the viscosity of the coating formulation may also vary depending on the application method and/or type of solvent employed. The viscosity is typically, however, from about 1 to about 200 Pascal-seconds, in some embodiments from about 5 to about 150 Pascal-seconds, and in some embodiments, from about 10 to about 100 Pascal-seconds, as measured with a Brookfield DV-1 viscometer using Spindle No. 18 operating at 12 rpm and 25° C. If desired, thickeners or other viscosity modifiers may be employed in the formulation to increase or decrease viscosity.

The coating formulation may be applied to a substrate using any conventional technique, such as printing, dipping, spraying, melt extruding, coating (e.g., solvent coating, powder coating, brush coating, etc.), and so forth. In one embodiment, for example, the ink is printed onto the substrate. A variety of printing techniques may be used for applying the ink to the support, such as gravure printing, flexographic printing, screen printing, laser printing, thermal ribbon printing, piston printing, etc. In one particular embodiment, ink-jet printing techniques are employed to apply the ink to the substrate. Ink-jet printing is a non-contact printing technique that involves forcing an ink through a tiny nozzle (or a series of nozzles) to form droplets that are directed toward the support. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically. Thus, when the sample channel is formed from a dielectric material, DOD printing techniques may be more desirable.

The coating formulation may be applied to one or both surfaces of the substrate. For example, the resulting ink is generally present on at least the surface of the substrate that is likely to contact bodily fluids during use. In addition, the ink may cover an entire surface of the substrate, or may only cover a portion of the surface. When applying the ink to multiple surfaces, each surface may be coated sequentially or simultaneously. Regardless of the manner in which it is applied, the resulting substrate may be dried at a certain temperature to drive the solvent from the formulation and form the ink of the present invention. For example, the substrate may be dried at a temperature of at least about 20° C., in some embodiments at least about 25° C., and in some embodiments, from about 25° C. to about 75° C. Minimizing the amount of solvent in the ink allows the chromogen to initially remain in its deprotonated state. Nevertheless, it should be understood that some solvent may still be present. For example, the ink may contain a solvent in an amount less than about 0.5% by weight, in some embodiments less than about 0.1% by weight, and in some embodiments, less than about 0.01% by weight.

Any of a variety of different substrates may be incorporated with the ink of the present invention. For instance, nonwoven webs, woven fabrics, knit fabrics, paper webs, films, foams, strands, etc., may be applied with the ink. When utilized, the nonwoven webs may include, but are not limited to, spunbonded webs (apertured or non-apertured), meltblown webs, bonded carded webs, air-laid webs, coform webs, hydraulically entangled webs, and so forth. Nonwoven composites (e.g., nonwoven web laminated to a film or strands) may also be employed. Typically, the polymers used to form the substrate have a softening or melting temperature that is higher than the temperature needed to remove the solvent from the ink. One or more components of such polymers may have, for instance, a softening temperature of from about 100° C. to about 400° C., in some embodiments from about 110° C. to about 300° C., and in some embodiments, from about 120° C. to about 250° C. Examples of such polymers may include, but are not limited to, synthetic polymers (e.g., polyethylene, polypropylene, polyethylene terephthalate, nylon 6, nylon 66, KEVLAR®), syndiotactic polystyrene, liquid crystalline polyesters, etc.); cellulosic polymers (softwood pulp, hardwood pulp, thermomechanical pulp, etc.); combinations thereof; and so forth.

The thickness of the ink may also vary. For example, the thickness may range from about 0.001 millimeters to about 3 millimeters, in some embodiments, from about 0.01 millimeters to about 2 millimeters, and in some embodiments, from about 0.01 millimeters to about 1 millimeter. Such a relatively thin ink may enhance the flexibility of the substrate, while still providing the desired color change.

To maintain absorbency, porosity, flexibility, and/or some other characteristic of the substrate, it may sometimes be desired to apply the ink so as to cover less than 100%, in some embodiments from about 10% to about 80%, and in some embodiments, from about 20% to about 60% of the area of one or more surfaces of the substrate. For instance, in one particular embodiment, the ink is applied to the substrate in a preselected pattern (e.g., reticular pattern, diamond-shaped grid, dots, and so forth). Although not required, such a patterned ink may provide a sufficient color change without covering a substantial portion of the surface area of the substrate. This may be desired to optimize flexibility, absorbency, or other characteristics of the substrate. It should be understood, however, that the ink may also be applied uniformly to one or more surfaces of the substrate. In addition, a patterned ink may also provide different functionality to each zone. For example, in one embodiment, the substrate is treated with two or more patterns of coated regions that may or may not overlap. The regions may be on the same or different surfaces of the substrate. In one embodiment, one region of a substrate is coated with a first ink, while another region is coated with a second ink.

If desired, the ink may also be applied to a strip that is subsequently adhered or otherwise attached to the substrate of the absorbent article. For example, the strip may contain a facestock material commonly employed in the manufacture of labels, such as paper, polyester, polyethylene, polypropylene, polybutylene, polyamides, etc. An adhesive, such as a pressure-sensitive adhesive, heat-activated adhesive, hot melt adhesive, etc., may be employed on one or more surfaces of the facestock material to help adhere it to a surface of the substrate. Suitable examples of pressure-sensitive adhesives include, for instance, acrylic-based adhesives and elastomeric adhesives. In one embodiment, the pressure-sensitive adhesive is based on copolymers of acrylic acid esters (e.g., 2-ethyl hexyl acrylate) with polar co-monomers (e.g., acrylic acid). The adhesive may have a thickness in the range of from about 0.1 to about 2 mils (2.5 to 50 microns).

As noted above, for example, the ink may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

Generally speaking, the wetness sensor of the present invention may be incorporated into the absorbent article in a variety of different orientations and configurations, so long as the device is capable of contacting bodily fluids and providing a signal to a user or caregiver. For example, the wetness sensor may be located on the bodyside liner, surge layer, absorbent core, outer cover, etc. In this regard, various embodiments of an absorbent article that may be formed according to the present invention will now be described in more detail. For purposes of illustration only, the absorbent article is shown in FIG. 1 as a diaper 101. In the illustrated embodiment, the diaper 101 is shown as having an hourglass shape in an unfastened configuration. However, other shapes can of course be utilized, such as a generally rectangular shape, T-shape, or I-shape. As shown, the diaper 101 includes a chassis formed by various components, including an outer cover 117, bodyside liner 105, absorbent core 103, and surge layer 107. It should be understood, however, that other layers can also be used in exemplary embodiments of the present disclosure. Likewise, one or more of the layers referred to in FIG. 1 can also be eliminated in certain exemplary embodiments.

The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. As indicated above, the liner 105 can be liquid-permeable to permit liquid to readily penetrate through its thickness. Exemplary liner constructions that contain a nonwoven web are described in U.S. Pat. No. 5,192,606 to Proxmire, et al.; U.S. Pat. No. 5,702,377 to Collier, I V. et al.; U.S. Pat. No. 5,931,823 to Stokes, et al.; U.S. Pat. No. 6,060,638 to Paul, et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The diaper 101 can also include a surge layer 107 that helps to decelerate and diffuse surges or gushes of liquid that can be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface of the bodyside liner 105 and the absorbent core 103. Alternatively, the surge layer 107 can be located on an outwardly facing surface 118 of the bodyside liner 105. The surge layer 107 is typically constructed from highly liquid-permeable materials. Examples of suitable surge layers are described in U.S. Pat. No. 5,486,166 to Bishop, et al. and U.S. Pat. No. 5,490,846 to Ellis, et al., which are incorporated herein in their entirety by reference thereto for all purposes.

The outer cover 117 is typically formed from a material that is substantially impermeable to liquids. For example, the outer cover 117 can be formed from a thin plastic film or other flexible liquid-impermeable material. In one embodiment, the outer cover 117 is formed from a polyethylene film having a thickness of from about 0.01 millimeter to about 0.05 millimeter. The film can be impermeable to liquids, but permeable to gases and water vapor (i.e., "breathable"). This permits vapors to escapee from the absorbent core 103, but still prevents liquid exudates from passing through the outer cover 117. If a more cloth-like feeling is desired, the outer cover 117 can be formed from a polyolefin film laminated to a nonwoven web. For example, a stretch-thinned polypropylene film can be thermally laminated to a spunbond web of polypropylene fibers. In the illustrated embodiment, a wetness sensor 140 is located on a body-facing surface 205 of the outer cover 117, such as adjacent to a nonwoven web or film of a composite used to form the cover 117. If desired, a transparent or translucent portion (e.g., window, film, etc.) may be employed to allow the sensor 140 to be readily viewed without removal of the absorbent article from the wearer and/or without disassembly. In other embodiments, the sensor 140 can extend through a hole or aperture in the absorbent article for observation.

Besides the above-mentioned components, the diaper 101 can also contain various other components as is known in the art. For example, the diaper 101 can also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet can be configured to provide a wicking layer that helps to rapidly distribute liquid over the mass of absorbent fibers of the absorbent core 103. The wrapsheet material on one side of the absorbent fibrous mass can be bonded to the wrapsheet located on the opposite side of the fibrous mass to effectively entrap the absorbent core 103. Furthermore, the diaper 101 can also include a ventilation layer (not shown) that is positioned between the absorbent core 103 and the outer cover 117. When utilized, the ventilation layer can help insulate the outer cover 117 from the absorbent core 103, thereby reducing dampness in the outer cover 117. Examples of such ventilation layers can include a nonwoven web laminated to a breathable film, such as described in U.S. Pat. No. 6,663,611 to Blaney, et al., which is incorporated herein in its entirety by reference thereto for all purposes.

In some embodiments, the diaper 101 can also include a pair of side panels (or ears) (not shown) that extend from the side edges 132 of the diaper 101 into one of the waist regions. The side panels can be integrally formed with a selected diaper component. For example, the side panels can be integrally formed with the outer cover 117 or from the material employed to provide the top surface. In alternative configurations, the side panels can be provided by members connected and assembled to the outer cover 117, the top surface, between the outer cover 117 and top surface, or in various other configurations. If desired, the side panels can be elasticized or otherwise rendered elastomeric by use of the elastic nonwoven composite of the present disclosure. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, et al., each of which is incorporated herein in its entirety by reference thereto for all purposes.

As representatively illustrated in FIG. 1, the diaper 101 can also include a pair of containment flaps 112 that are configured to provide a barrier and to contain the lateral flow of body exudates. The containment flaps 112 can be located along the laterally opposed side edges 132 of the bodyside liner 105 adjacent the side edges of the absorbent core 103. The containment flaps 112 can extend longitudinally along the entire length of the absorbent core 103, or can only extend partially along the length of the absorbent core 103. When the containment flaps 112 are shorter in length than the absorbent core 103, they can be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704,116 to Enloe, which is incorporated herein in its entirety by reference thereto for all purposes.

To provide improved fit and to help reduce leakage of body exudates, the diaper 101 can be elasticized with suitable elastic members, as further explained below. For example, as representatively illustrated in FIG. 1, the diaper 101 can include leg elastics 106 constructed to operably tension the side margins of the diaper 101 to provide elasticized leg bands which can closely fit around the legs of the wearer to reduce leakage and provide improved comfort and appearance. Waist elastics 108 can also be employed to elasticize the end margins of the diaper 101 to provide elasticized waistbands. The waist elastics 108 are configured to provide a resilient, comfortably close fit around the waist of the wearer. The diaper 101 can also include one or more fasteners 130. For example, two flexible fasteners 130 are illustrated in FIG. 1 on opposite side edges of waist regions to create a waist opening and a pair of leg openings about the wearer. The shape of the fasteners 130 can generally vary, but can include, for instance, generally rectangular shapes, square shapes, circular shapes, triangular shapes, oval shapes, linear shapes, and so forth. The fasteners can include, for instance, a hook-and-loop material, buttons, pins, snaps, adhesive tape fasteners, cohesives, fabric-and-loop fasteners, etc. In one particular embodiment, each fastener 130 includes a separate piece of hook material affixed to the inside surface of a flexible backing.

The various regions and/or components of the diaper 101 can be assembled together using any known attachment mechanism, such as adhesive, ultrasonic, thermal bonds, etc. Suitable adhesives can include, for instance, hot melt adhesives, pressure-sensitive adhesives, and so forth. When utilized, the adhesive can be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 can be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, can also be assembled into the diaper 101 using any attachment mechanism.

Figure 2:
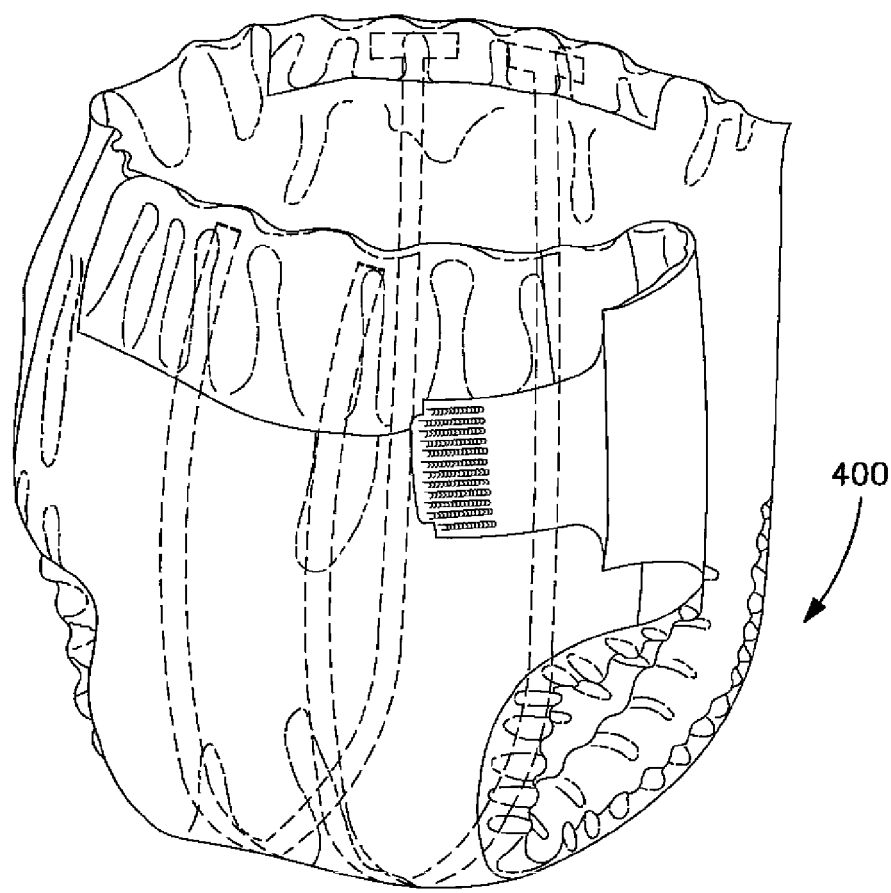
FIG. 2 is a perspective view of another embodiment of an absorbent article that may be used in conjunction with the wetness sensor of the present invention.

Although various configurations of a diaper have been described above, it should be understood that other diaper and absorbent article configurations are also included within the scope of the present invention. In addition, the present invention is by no means limited to diapers. In fact, several examples of absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Other examples of personal care products that may incorporate the wetness sensor of the present invention include training pants (such as in side panel materials) and feminine care products. By way of illustration only, FIG. 2 shows one embodiment of training pants 400 that may contain a wetness sensor (not shown). The training pants may be constructed from material and methods such as described above. Various other materials and methods for constructing training pants are also described U.S. Pat. No. 6,761,711 to Fletcher et al.; U.S. Pat. No. 4,940,464 to Van Gompel et al.; U.S. Pat. No. 5,766,389 to Brandon et al.; and U.S. Pat. No. 6,645,190 to Olson et al., which are incorporated herein in their entirety by reference thereto for all purposes.

The present invention may be better understood with reference to the following examples.

EXAMPLE 1

Violet Lactone II was dissolved in an ethanol solution at a concentration of 200 milligrams of the dye per milliliter of ethanol, 50 microliters of the dye solution was then mixed with 200 microliters of citric acid (100 milligrams per milliliter in ethanol). Thereafter, 20 microliters of the citric acid/dye solution was mixed with either 10 microliters of "940-1021" varnish from SunChemical (10 wt. % in ethanol) ("Sample A"); 10 microliters of "CASPER" varnish from SunChemical (10 wt. % in ethanol) ("Sample B"); or a mixture of 10 microliters of "940-1021" varnish (10 wt. % in ethanol) and 10 microliters of "CASPER" varnish (10 wt. % in ethanol) ("Sample C"). Samples A, B, and C were then separately applied to the outer cover of a PULL UP® diaper (Kimberly-Clark) and air dried. The color of the coated substrate was recorded. 10 microliters of water was then dropped on the coated substrate and observed. The color of the coated substrates was then recorded immediately after contacting the water. The results are set forth below:

|   | Sample | Color Change |
|---|---|---|
| A | Before contact with water | Pink Red |
|   | After contact with water | Colorless |
| B | Before contact with water | Pink Red |
|   | After contact with water | Colorless |
| C | Before contact with water | Pink Red |
|   | After contact with water | Colorless |

EXAMPLE 2

1 milligram of Violet Lactone II and 10 milligrams of citric acid were dissolved in 50 microliters of ethanol. To this solution was added 100 microliters of cellulose acetate butyrate (CAB-553 from Eastman Kodak of Kingsport, Tenn.) in a solution of ethanol/n-propyl acetate (1:1 wt. ratio) at a concentration of 0.1 gram per milliliter. 30 microliters of the resulting dye solution was then applied to the outer cover of a PULL UP® diaper (Kimberly-Clark) and air dried. The color of the coated substrate was pink red. 10 microliters of water was then dropped on the coated substrate. The coated substrate became colorless immediately after contacting the water.

EXAMPLE 3

1 milligram of Violet I and 10 milligrams of citric acid were dissolved in 150 microliters of ethanol. To this solution was added 100 microliters of cellulose acetate butyrate (CAB-553 from Eastman Kodak of Kingsport, Tenn.) in a solution of ethanol/n-propyl acetate (1:1 wt. ratio) at a concentration of 0.1 gram per milliliter. 30 microliters of the resulting dye solution was then applied to the outer cover of a PULL UP® diaper (Kimberly-Clark) and air dried. The color of the coated substrate was blue. 10 microliters of water was then dropped on the coated substrate. The coated substrate became colorless immediately after contacting the water.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article comprising:
a substantially liquid impermeable layer;
a liquid permeable layer;
an absorbent core positioned between the substantially liquid impermeable layer and the liquid permeable layer; and
a wetness sensor integrated into the article and positioned such that the sensor is in fluid communication with a bodily fluid from a wearer of the article, wherein the wetness sensor includes an ink comprising a proton-accepting chromogen and a proton-donating agent, wherein the proton-donating agent includes an aliphatic carboxylic acid, the weight ratio of the proton-donating agent to the proton-accepting chromogen being from about 0.4 to about 10, wherein the ink undergoes a visible color change upon contact with the bodily fluid, further wherein the ink is free of wetting agents.

2. The absorbent article of claim 1, wherein the aliphatic carboxylic acid exhibits a solubility in water of greater than about 5 grams per 100 milliliters of water at a temperature of 20° C.

3. The absorbent article of claim 1, wherein the aliphatic carboxylic acid exhibits a solubility in water of from about 30 to about 200 grams per 100 milliliters of water at a temperature of 20° C.

4. The absorbent article of claim 1, wherein the aliphatic carboxylic acid has a first acid dissociation constant of about 0.5 to about 6.

5. The absorbent article of claim 1, wherein the aliphatic carboxylic acid is polyprotic.

6. The absorbent article of claim 1, wherein the aliphatic carboxylic acid includes acrylic acid, methacrylic acid, malonic acid, succinic acid, adipic acid, maleic acid, malic acid, oleic acid, tartaric acid, citric acid, formic acid, acetic acid, glycolic acid, oxalic acid, propionic acid, glutaric acid, gluconic acid, lactic acid, aspartic acid, glutaminic acid, itaconic acid, trifluoroacetic acid, or a mixture thereof.

7. The absorbent article of claim 1, wherein the aliphatic carboxylic acid is a polymeric acid.

8. The absorbent article of claim 1, wherein the proton-accepting chromogen is a leuco dye that is generally colorless when deprotonated.

9. The absorbent article of claim 1, wherein the proton-accepting chromogen includes a phthalide, phthalene, acyl-leucomethylene, fluorane, spiropyrane, cumarin, or a combination thereof.

10. The absorbent article of claim 1, wherein the weight ratio of the proton-donating agent to the proton-accepting chromogen is from about 1 to about 4.

11. The absorbent article of claim 1, wherein the ink further comprises an organic binder.

12. The absorbent article of claim 1, wherein the ink further comprises a macromolecular anchoring compound.

13. The absorbent article of claim 1, wherein the wetness sensor is disposed on the substantially liquid-impermeable layer.

14. The absorbent article of claim 13, wherein the substantially liquid-impermeable layer is a nonwoven composite formed from a nonwoven web laminated to a film.

15. The absorbent article of claim 1, wherein the wetness sensor further comprises a substrate on which the ink is disposed, wherein the substrate is integrated into the absorbent article.

16. An absorbent article comprising a wetness sensor that includes an ink disposed on a substrate, wherein the ink comprises a leuco dye and a proton-donating agent, the proton-donating agent including an aliphatic carboxylic acid having a solubility in water of greater than about 5 grams per 100 milliliters of water at a temperature of 20° C. and a first acid dissociation constant of from about 0 to about 8, the weight ratio of the proton-donating agent to the leuco dye being from about 0.4 to about 10, wherein the ink undergoes a visible color change upon contact with an aqueous fluid, further wherein the ink is free of wetting agents.

17. The absorbent article of claim 16, wherein the aliphatic carboxylic acid exhibits a solubility in water of from about 30 to about 200 grams per 100 milliliters of water at a temperature of 20° C.

18. The absorbent article of claim 16, wherein the aliphatic carboxylic acid has a first acid dissociation constant of about 0.5 to about 6.

19. The absorbent article of claim 16, wherein the aliphatic carboxylic acid is polyprotic.

20. The absorbent article of claim 16, wherein the aliphatic carboxylic acid includes acrylic acid, methacrylic acid, malonic acid, succinic acid, adipic acid, maleic acid, malic acid, oleic acid, tartaric acid, citric acid, formic acid, acetic acid, glycolic acid, oxalic acid, propionic acid, glutaric acid, gluconic acid, lactic acid, aspartic acid, glutaminic acid, itaconic acid, trifluoroacetic acid, or a mixture thereof.

21. The absorbent article of claim 16, wherein the aliphatic carboxylic acid is a polymeric acid.

22. The absorbent article of claim 16, wherein the leuco dye includes a phthalide, phthalene, acyl-leucomethylene, fluorane, spiropyrane, cumarin, or a combination thereof.

23. The absorbent article of claim 16, wherein the weight ratio of the proton-donating agent to the leuco dye is from about 1 to about 4.

24. The absorbent article of claim 16, wherein the ink further comprises an organic binder.

25. A wetness sensor for an absorbent article that comprises an ink disposed on a substrate, wherein the ink comprises a leuco dye and a proton-donating agent, the proton-donating agent including an aliphatic carboxylic acid having a solubility in water of greater than about 5 grams per 100 milliliters of water at a temperature of 20° C. and a first acid dissociation constant of from about 0 to about 8, the weight ratio of the proton-donating agent to the leuco dye being from about 0.4 to about 10, wherein the ink undergoes a visible color change upon contact with an aqueous fluid, further wherein the ink is free of wetting agents.

\* \* \* \* \*